United States Patent [19]

O'Hara

[11] Patent Number: 5,352,227
[45] Date of Patent: Oct. 4, 1994

[54] INTERCALARY DEVICE

[75] Inventor: April L. O'Hara, Basking Ridge, N.J.

[73] Assignee: Howmedica Inc., New York, N.Y.

[21] Appl. No.: 13,592

[22] Filed: Feb. 3, 1993

[51] Int. Cl.⁵ .............................................. A61F 2/28
[52] U.S. Cl. ........................................ 606/63; 606/62; 606/68
[58] Field of Search ....................... 606/57, 58, 62, 63, 606/68, 70, 71

[56] References Cited

U.S. PATENT DOCUMENTS

| 3,244,170 | 4/1966 | McElvenny | 606/71 |
|---|---|---|---|
| 3,680,553 | 8/1972 | Seppo . | |
| 3,900,025 | 8/1975 | Barnes, Jr. | 606/71 |
| 4,016,874 | 4/1977 | Maffei et al. . | |
| 4,157,715 | 6/1979 | Westerhoff . | |
| 4,190,044 | 2/1980 | Wood | 606/63 |
| 4,262,665 | 4/1981 | Roalstad et al. . | |
| 4,384,373 | 5/1983 | Sivash . | |
| 4,453,539 | 6/1984 | Raftopoulos et al. . | |
| 4,502,160 | 3/1985 | Moore et al. . | |
| 4,629,463 | 12/1986 | Grundei et al. | 606/62 |
| 4,764,171 | 8/1988 | Harder et al. | 623/20 |
| 4,892,546 | 1/1990 | Kotz et al. | 623/18 |
| 5,074,882 | 12/1991 | Grammont et al. | 623/23 |
| 5,122,141 | 6/1992 | Simpson et al. | 606/63 |
| 5,190,544 | 3/1993 | Chapman et al. | 606/71 |

FOREIGN PATENT DOCUMENTS

| 2657303 | 6/1977 | Fed. Rep. of Germany | 606/62 |
|---|---|---|---|
| 2137884 | 10/1984 | United Kingdom . | |

Primary Examiner—Stephen C. Pellegrino
Assistant Examiner—J. A. Schmidt
Attorney, Agent, or Firm—Peter C. Richardson; Lawrence C. Akers; Raymond W. Augustin

[57] ABSTRACT

A kit for coupling two bone segments has a first longitudinally extending intercalary element with a first end for insertion into the medullary canal of one of the bone segments and a second end in the form of a male conically tapered section, The kit also has a second longitudinally extending intercalary element having a first end for insertion into the medullary canal of the other bone segment which element has a second end in the form of a female conically tapered section for mating with the male section of the first intercalary element, Both intercalary elements have engagement elements formed thereon intermediate the first and second ends thereof. An instrument is provided having a pair of movable arms for engaging a respective one of the engagement elements formed on the intercalary elements, The arms may be moved towards or away from one another after engaging the engagement elements formed on the intercalary elements, The instrument thus moves the male and female conically tapered sections towards or away from one another in the longitudinal directions to either couple or uncouple the first and second intercalary elements. Elongation elements are optionally provided to be inserted between the intercalary elements to expand the length of the bone into which they are inserted.

4 Claims, 3 Drawing Sheets

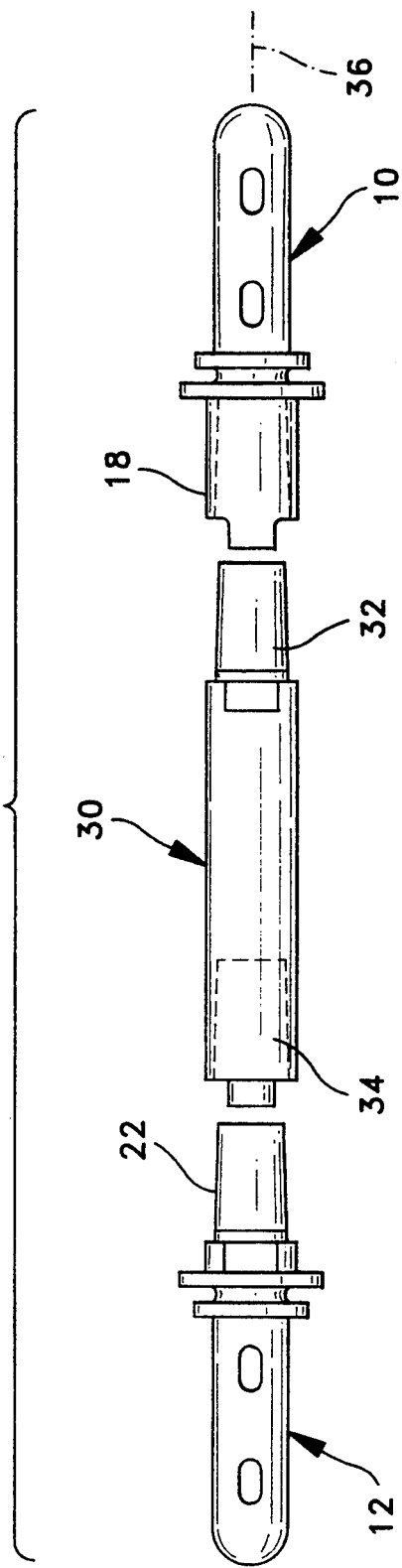
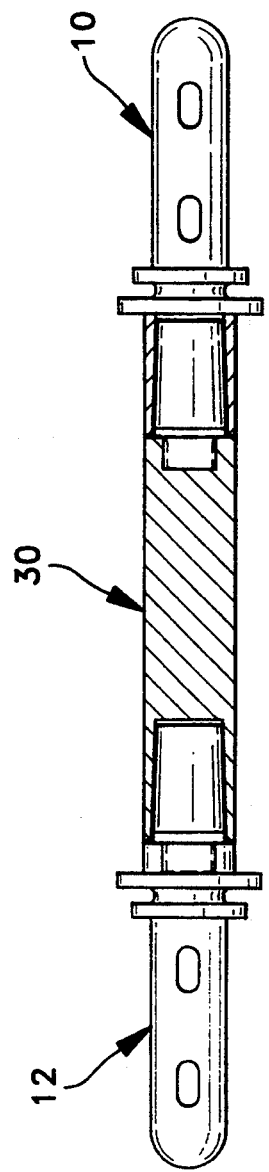

INTERCALARY DEVICE

BACKGROUND OF THE INVENTION

1. Field of the Invention

The invention relates to the medical techniques for prostheses used in orthopedic surgery, and more particularly to surgical implants for connecting two bone segments and/or for lengthening limbs or of the extremities.

More particularly, the invention relates to an expandable intramedullary nail disposed inside a patient and configured for insertion into a medullary cavity of the patient's limb containing a bone and is designed to be expandable intraoperatively, if desired, by simple assembly and disassembly with an expandable prosthesis engagement instrument.

2. Description of the Prior Art

It is known that after congenital malformations or anomalies, or even after fractures, losses of osseous or other substances, certain bones such as the humerus, femur, tibia, etc., are too short, thus creating asymmetry or hypometry. In the case of lower limbs with slight asymmetry, less than 3 centimeters, orthopedic treatment is called for by adding, for example, a shoe or other orthopedic apparatus to the limb which is short. With asymmetry or hypometry which is more significant, in order to elongate the short limb, surgical solutions currently using two types of means exist:

External fixtures—an operation is performed using external apparatus on certain parts of which, for example, metal pins, etc., go through the soft tissues to reach the bone of which they are an integral part. The apparatus can be seen from outside the limb. The advantage of such apparatus which is therefore accessible from the outside is that a physician can act on the apparatus at determined periods of time in order to consequently provoke a certain degree of elongation of the bone in a progressive manner, generally at the diaphysis of the bone after cutting the latter.

Internal fixtures—the second solution consists of taking action from the inside, i.e., no element can be seen from outside the limb. For this purpose, centromedullary nails or intramedullary nails are generally used or osteosynthesis plates which are suitably fixed to the bone.

The advantage of this solution with respect to the previous one lies in the fact that no element can be seen from outside the limb. On the other hand, the bone cannot be progressively elongated, which may be required for a growing child. However, a quite significant elongation can be carried out thanks to repeated surgical interventions which are consistent each time in obtaining a fixed but limited elongation due to elastic and plastic limits of the soft tissues on stretching. In the case of non-progressive significant elongation, the compensation of the dimensional deviation is risky and requires adjuvants to the osteosynthesis, i.e., grafts, etc., which reduce the mechanical and physiological properties of the elongated bone.

Currently there is no elongatable nail which can be easily assembled and disassembled while still fixed to each bone segment it is aligning.

Various prior art intramedullary nails, and the like, as well as apparatus and method of their construction in general, are known, and exemplary of this prior art are the following patents:

| | |
|---|---|
| Seppo | 3,680,553 |
| Westerhoff | 4,157,715 |
| Roalstad | 4,262,665 |
| Sivash | 4,384,373 |
| Raftopoulos | 4,453,539 |
| Moore | 4,502,160 |
| Kotz | 4,764,171 |
| Kotz | 4,892,546 |
| Grammart | 5,074,882 |
| Keller | EP 0212192 |
| Scales | GB 2137884 A |
| Bauman | DE 02705154 A1 |

The device of Seppo is a fixing apparatus for osteosynthesis of fractures and includes a complex mechanism that does not feature a lengthening function. Westerhoff can be considered as a lengthening device effected solely by means of a small pump which is set out of the cylindrical device. Roalstad does not feature a lengthening function, but is an intramedullary compression device set during the surgical procedure and not capable of being modified thereafter. Raftopoulos discloses an expandable intramedullary device having an expandable part acting as a locker in the bone, and has no lengthening function.

SUMMARY OF THE INVENTION

The object of the invention is to provide an expandable intercalary system in which a pair of intercalary elements having conically tapered sections may join two segments of bone.

It is a further object of the invention to provide an instrument which facilitates the moving apart and joining together of the two intercalary elements while each is affixed to the bone so that, if desired, an expandable piece can be inserted in between.

These and other objects of the invention are provided by a kit for coupling two bone segments together. The kit consists of a first longitudinally extending intercalary element having a first end for insertion into the medullary canal of one of the bone segments, and a second end in the form of male conically tapered section. A second longitudinally extending intercalary element is provided having a first end for insertion into the medullary canal of the other bone segment and having a second end in the form of a female conically tapered section for mating with the male section of the first intercalary element to thereby couple the bone segments together. Both the first and second longitudinally extending intercalary elements have engagement elements formed thereon intermediate the first and second ends thereof.

An instrument having a pair of movable arms is provided for engaging a respective one of the engagement elements formed on the intercalary elements. Upon engagement, the instrument can move the male and female conically tapered sections towards or away from one another in the longitudinal direction to couple or uncouple the first and second intercalary elements.

The kit may also contain at least one extension element having a male conically tapered section at a first end and a female conically tapered section at a second end. These conically tapered sections are sized to mate with the respective ends of the intercalary elements for increasing the distance between the bone segments coupled by the intercalary elements. The instrument is able to be adjusted in the longitudinal direction so that the arms thereon may still engage the engagement elements on each intercalary element, even in an expanded position.

The instrument for joining the two intercalary elements includes a rod having a first section with a right hand externally threaded portion and a second section having a left hand externally threaded portion. The instrument includes a first arm for engaging one of the elements threadably mounted on the threaded portion of the first section. A second arm is provided for engaging the other of the intercalary elements, which arm is threadably mounted on the threaded portion of the second section so that upon rotation of the rod in either direction, the first and second arms move respectively towards or away from one another.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views:

FIG. 3 is an exploded view of the intercalary elements of FIG. 1 with an extension element located therebetween;

FIG. 4 shows the intercalary elements and extension piece of FIG. 3 in an assembled position;

DESCRIPTION OF THE PREFERRED EMBODIMENTS

Figure 1:
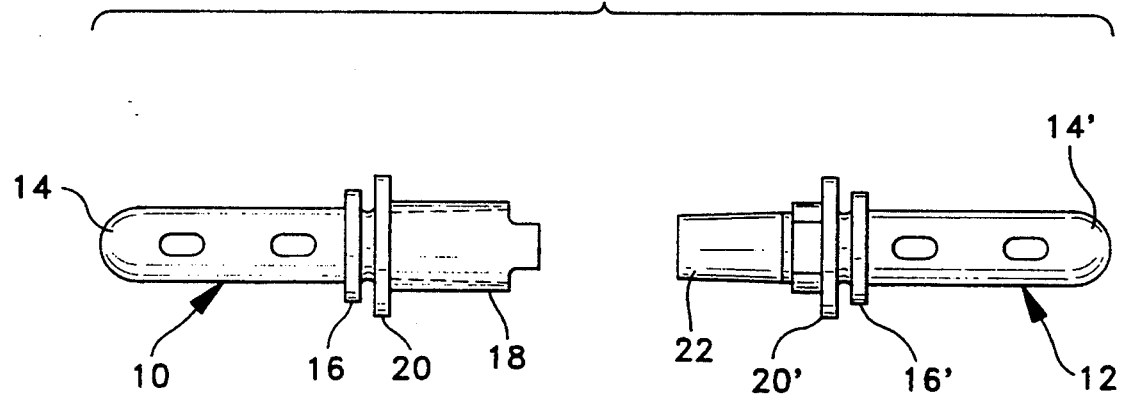
FIG. 1 is an exploded view of the male and female intercalary elements of the present invention.

Referring to FIG. 1 there is shown a female intercalary element generally denoted at 10 and a male intercalary element generally denoted as 12. Each of the intercalary elements 10, 12 include a first end 14, 14' respectively extending from a flanged portion 16, 16'. Intercalary element 10 has a conically tapered female portion 18 at a second end thereof extending from a flange 20. Intercalary element 12 includes a conically tapered male portion 22 extending from a flange 20'.

Figure 2:
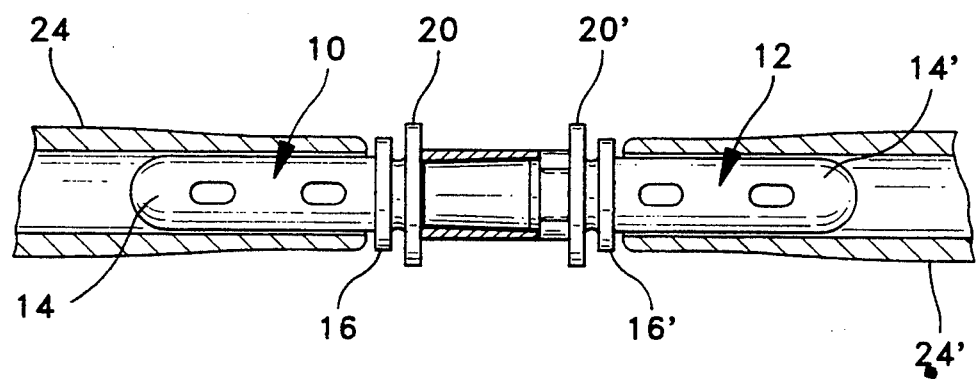
FIG. 2 is a view of the intercalary elements of FIG. 1 in an assembled position with a first end of each intercalary element within a medullary canal of the bone.

Referring to FIG. 2 there is shown the intercalary elements 10 and 12 of FIG. 1 in an assembled position with ends 14, 14' embedded within a pair of bone segments 24 and 24'. As can be seen, flanges 16, 16' sit on the prepared ends of bone segments 24, 24'.

Referring to FIG. 3 there is shown intercalary elements 1 0, 12 identical to that described with respect to FIG. 1. While the intercalary elements of FIG. 1 may be used to join bone segments together, the addition of an extension element generally denoted as 30 allows for the lengthening of the distance between bone segments 24, 24'. Extension element 30 includes a conically tapered male portion 32 at one end thereof and a conically tapered female portion 34 at the other end thereof. The conically tapered sections 32 and 34 are longitudinally aligned along axis 36 with female conical portion 18 of intercalary element 10 and conically tapered male portion 22 of intercalary element 12.

Referring to FIG. 4 there is shown the expandable intercalary device of FIG. 3 in an assembled position.

Figure 5:
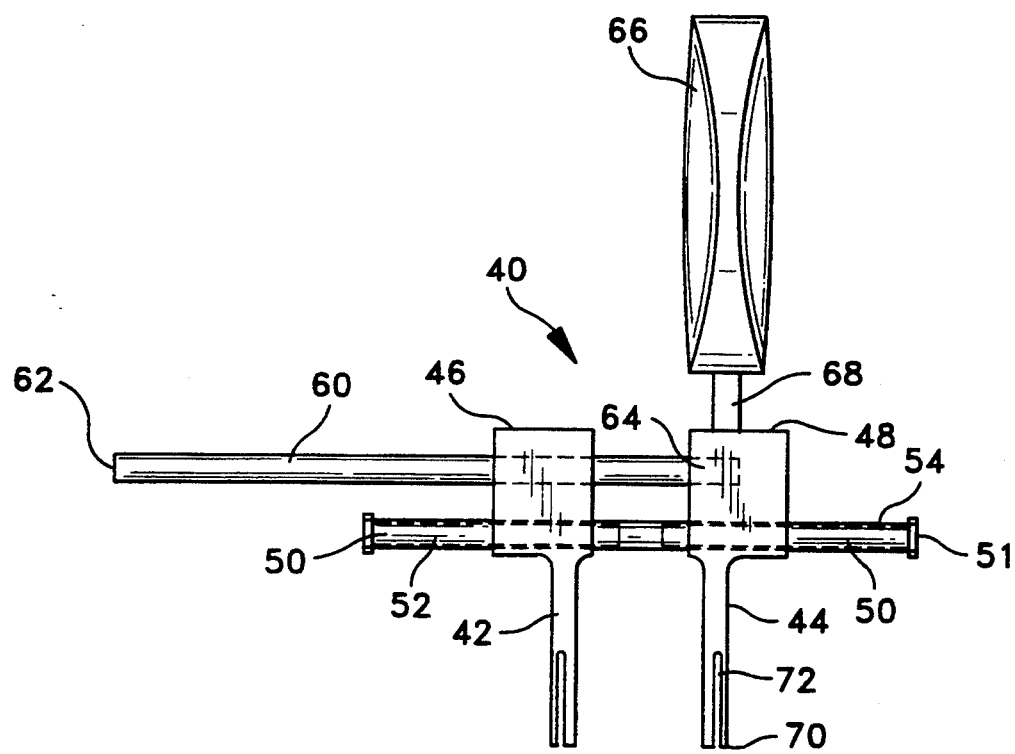
FIG. 5 is an instrument having a pair of arms for engaging both the male and female intercalary elements of FIG. 1 and moving them towards or away from one another.
Figure 6:
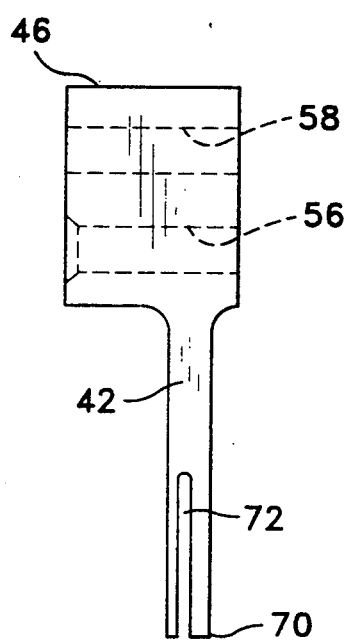
FIG. 6 is an enlarged view of the left hand arm shown in FIG. 5.
Figure 7:
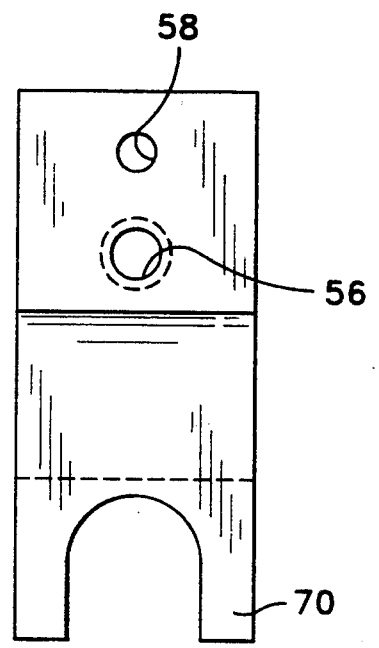
FIG. 7 is a side view of the arm shown in FIG. 6.

Referring to FIGS. 5-7 there is shown a preferred embodiment of the instrument of the present invention generally denoted as 40 having a pair of arms 42, 44. In the preferred embodiment arms 42, 44 include body portions 46 and 48 mounted on a threaded rod 50. Rod 50 has a right hand threaded portion 52 and a left hand threaded portion 54. Rod 50 includes a hex portion 51 at each end for accommodating a drive tool (not shown). The preferred bodies 46, 48 both include a threaded aperture 56. The threaded aperture 56 of body 46 mounts on threaded portion 52 and the threaded aperture 56 of body portion 48 is threaded onto threaded portion 54 of rod 50.

In the preferred embodiment body 46 has a second non-threaded aperture 58 therethrough for mounting on a guide rod 60 having a free end 62 and an end 64 rigidly coupled to body 48 and thus integral therewith. Rod 60 serves to prevent rotation of arms 42, 44 with respect to rod 50.

Body 48 further includes a handle 66 rigidly coupled thereto via shaft 68.

Referring to FIGS. 6 and 7 there is shown left hand body 46 and arm 42 of FIG. 5. In the preferred embodiment body 48 and arm 44 are identical to body 46 and arm 42 with the exception that aperture 58 is eliminated. Arms 42, 44 include a U-shaped end portion 70 having a slot 72 formed therein. Slot 72 is adapted to fit over and capture flanges 20, 20' of intercalary device 10, 12 respectively.

The use of the system for reconstructive procedures or for intercalary bone segment coupling will now be described. First, as shown in FIG. 2, ends 14, 14' of intercalary devices 10, 12 respectively are inserted into the open ends of bone segments 24, 24'. This can be done with bone cement or by providing tissue ingrowth surfaces on the elements 10, 12 in the area between ends 14, 14' and flanges 16, 16'. Intercalary elements 10, 12 are then moved into close proximity and a slot 70 on arms 42, 44 is slid over their respective flanges 20, 20'. Rod 50 is then rotated in the direction which moves arms 42 and 44 towards one another via a tool (not shown) placed on hex head 51 of rod 50.

If after a period of time after implantation elongation of the bone is deemed necessary, a second operation can be performed on the patient and slot 70 of arms 42, 44 of instrument 40 may be placed over respective flanges 20, 20'. Rod 50 is then rotated in a direction which moves arms 42, 44 apart a sufficient distance to allow insertion of an extension element 30 therebetween. The length of rod 50 is sufficient so that even in the expanded position, slot 70 of arms 42, 44 may again engage flanges 20, 20' and move conically tapered portions 18, 20, 32 and 34 into engagement. It can be seen that extension element 30 may be provided in any length and in the preferred kit of the present invention a series of expansion elements 30 are provided so that progressive bone elongation can be accomplished.

While several examples of the present invention have been described, it is obvious that many changes and modifications may be made thereunto, without departing from the spirit and scope of the invention.

I claim:

1. A kit for coupling two bone segments comprising:
   a first longitudinally extending intercalary element having a first end for insertion into the medullary canal of one of the bone segments and a second end in the form of a male conically tapered portion;
   a second longitudinally extending intercalary element having a first end for insertion into the medullary canal of the other bone segment and having a second end in the form of a female conically tapered portion for mating with said male section of said first intercalary element to couple the bone segments;
   engagement means formed on each of said intercalary elements intermediate said first and second ends thereof, said engagement means having a flange formed thereon and extending radially outwardly from an outer surface intermediate the first and second ends thereof;
   an instrument having a pair of moveable arms each for engaging a respective one of said flange of said engagement means formed on each of said first and second intercalary elements for moving said male and female conically tapered portions towards or away from one another in the longitudinal direction to couple or uncouple said first and second intercalary elements; and
   at least one extension element having a male conically tapered portion at a first end and a female conically tapered portion at a second end, said conically tapered portions for mating with respective ends of said intercalary elements for increasing the distance between the bone segments coupled by said intercalary elements.

2. The kit as set forth in claim 1 wherein said instrument further comprises a body portion integral with each of said arms, said body portions having threaded apertures extending therethrough for threaded engagement with a threaded rod, said rod including a right hand threaded portion and a left hand threaded portion, said threaded aperture of each of said arms mounted on a respective threaded portion of said threaded rod so that upon rotation of said rod, said pair of arms moves towards or away from one another.

3. The kit as set forth in claim 2 wherein one of said body portions includes a non-threaded aperture and said instrument further comprises a guide shaft rigidly coupled to the other of said body portions and slidably received within the aperture of said one body portion.

4. An instrument for coupling and uncoupling two longitudinally extending intercalary elements of an inercalary device placed between two bone segments, a male conical locking taper portion formed on a first of the intercalary elements and a mating female conical locking taper portion on a second of the intercalary elements, said first and second intercalary elements each having a radially outwardly extending flange thereon, said instrument comprising:
   a rod extending along a longitudinal axis and having a first longitudinally extending portion with a right hand external thread and second longitudinally extending portion having a left hand external thread portion;
   a first arm having a slotted portion extending in a direction generally perpendicular to said longitudinal axis of said rod for engaging the flange on one of the first and second intercalary elements, said first arm threadably mounted on said thread of said first rod portion;
   a second arm having a slotted portion extending in a direction generally perpendicular to said longitudinal axis of said rod for engaging the flange on the other of the intercalary elements, said second arm threadably mounted on said thread of said second rod portion so that upon rotation of said rod in either direction, said first and second arms move towards or away from one another, each of said arms include a body portion having a threaded aperture for engagement with said first and second threaded portions on said rod, wherein a longitudinal axis of said guide shaft and the longitudinal axis of said rod extend parallel to a longitudinal axis extending through the male conical locking taper portions on the first intercalary element and the female conical locking taper portion on the second intercalary element when said arms are coupled to the outwardly extending flanges on the first and second intercalary elements; and
   a handle integral with the body portion that is rigidly coupled to said guide shaft and extending in a direction perpendicular to the longitudinal axis of said rod and said guide shaft.

* * * * *